US00PP33202P2

(12) United States Plant Patent
Meulenbroek

(10) Patent No.: US PP33,202 P2
(45) Date of Patent: Jun. 29, 2021

(54) STRAWBERRY PLANT NAMED 'VERDI'

(50) Latin Name: ***Fragaria* x *ananassa***
Varietal Denomination: Verdi

(71) Applicant: FRESH FORWARD HOLDING B.V., Eck en Wiel (NL)

(72) Inventor: Egbertus Joseph Meulenbroek, Zetten (NL)

(73) Assignee: Fresh Forward Holding B.V., Eck en Wiel (NL)

( * ) Notice: Subject to any disclaimer, the term of this patent is extended or adjusted under 35 U.S.C. 154(b) by 0 days.

(21) Appl. No.: 16/974,076

(22) Filed: Sep. 22, 2020

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of Strawberry plant named 'Verdi', characterized by its compact and upright plant habit; moderately vigorous growth habit; early and uniform fruit ripening; medium to large-sized conical fruits that are glossy and reddish orange in color; pleasant fruit aroma and sweet taste; and excellent fruit postharvest longevity.

2 Drawing Sheets

Botanical designation: *Fragaria* x *ananassa*.
Cultivar denomination: 'VERDI'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Fresh Forward Holding B.V. of Eck en Wiel, The Netherlands on Mar. 29, 2018, application number 2018/0902. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exemption under 35 U.S.C. 102(b)(1) for disclosure and/or sales prior to the filing date but less than one year prior to the effective filing date.

BACKGROUND OF THE INVENTION

The present Invention relates to a new and distinct cultivar of Strawberry plant, botanically known as *Fragaria* x *ananassa* and hereinafter referred to by the name 'Verdi'.

The new Strawberry plant is a product of a planned breeding program conducted by the Inventor in Eck en Wiel, The Netherlands. The objective of the breeding program was to develop new Strawberry plants with good fruit quality, ease of harvesting, high yield, large attractive fruits and good postharvest longevity.

The new Strawberry plant originated from a cross-pollination by the Inventor in March, 2011 in Eck en Wiel, The Netherlands of a proprietary selection of *Fragaria* x *ananassa* identified as code number E2008-001, not patented, as the female, or seed, parent with a proprietary selection of *Fragaria* x *ananassa* identified as code number E2006-367, not patented, as the male, or pollen, parent. The new Strawberry plant was discovered and selected by the Inventor as a single plant from within the progeny of the stated cross-pollination in a controlled environment in Eck en Wiel, The Netherlands in June, 2012.

Asexual reproduction of the new Strawberry plant by runner cuttings in a controlled environment at Eck en Wiel, The Netherlands since July, 2012 has shown that the unique features of this new Strawberry plant are stable and reproduced true to type in successive generations of asexual reproduction.

SUMMARY OF THE INVENTION

Plants of the new Strawberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Verdi'. These characteristics in combination distinguish 'Verdi' as a new and distinct Strawberry plant:

1. Compact and upright plant habit.
2. Moderately vigorous growth habit.
3. Early and uniform fruit ripening.
4. Medium to large-sized conical fruits that are glossy and reddish orange in color.
5. Pleasant fruit aroma and sweet taste.
6. Excellent fruit postharvest longevity.

Plants of the new Strawberry differ primarily from plants of the female parent selection in the following characteristics:

1. Plants of the new Strawberry are more upright than and not as spreading as plants of the female parent selection.
2. Fruits of plants of the new Strawberry are conical in shape whereas fruits of plants of the female parent selection are cylindrical to rhomboid in shape.
3. With relation to their position to the fruits, sepals of plants of the new Strawberry are positioned more horizontal than and not as upright as sepals of plants of the female parent selection.

Plants of the new Strawberry differ primarily from plants of the male parent selection in the following characteristics:

1. Plants of the new Strawberry are more upright than and not as spreading as plants of the male parent selection.
2. Fruits of plants of the new Strawberry are reddish orange in color whereas fruits of plants of the male parent selection are more orange in color.
3. Seeds of plants of the new Strawberry are positioned level with the fruit surface whereas seeds of plants of the male are positioned slightly below the fruit surface.

Plants of the new Strawberry can be compared to plants of *Fragaria* x *ananassa* 'Clery', not patented. In side-by-side comparisons, plants of the new Strawberry differ primarily from plants of 'Clery' in the following characteristics:

1. Plants of the new Strawberry are more upright than and not as spreading as plants of 'Clery'.
2. Leaves of plants of the new Strawberry are darker green in color than leaves of plants of 'Clery'.
3. Plants of the new Strawberry have longer trusses than plants of 'Clery'.
4. Fruits of plants of the new Strawberry are conical in shape whereas fruits of plants of 'Clery' are cylindrical to rhomboid in shape.

Plants of the new Strawberry can be compared to plants of *Fragaria* x *ananassa* 'Elsanta', not patented. In side-by-side comparisons, plants of the new Strawberry differ primarily from plants of 'Elsanta' in the following characteristics:

1. Plants of the new Strawberry are more upright than and not as spreading as plants of 'Elsanta'.
2. Fruits of plants of the new Strawberry are conical in shape whereas fruits of plants of 'Elsanta' are cordate in shape.
3. Seeds of plants of the new Strawberry are positioned level with the fruit surface whereas seeds of plants of 'Elsanta' are positioned slightly below the fruit surface.

Plants of the new Strawberry can also be compared to plants of *Fragaria* x *ananassa* 'Allegro', disclosed in U.S. Plant Pat. No. 29,964. In side-by-side comparisons, plants of the new Strawberry differ primarily from plants of 'Allegro' in the following characteristics:

1. Plants of the new Strawberry are somewhat less vigorous than plants of 'Allegro'.
2. Plants of the new Strawberry have slightly larger flowers with broader calyxes than plants of 'Allegro'.
3. Plants of the new Strawberry produce heavier fruits than plants of 'Allegro'.
4. The fruit's flesh of plants of the new Strawberry is lighter reddish orange in color than the fruit's flesh of plants of 'Allegro'.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photograph on the first sheet is a top perspective view of typical flowering and fruiting plants of 'Verdi' grown in a greenhouse environment.

The photograph on the second sheet is a close-up view of typical flowering and fruiting plants of 'Verdi'.

DETAILED BOTANICAL DESCRIPTION

The following observations and measurements describe plants grown in beds and 2.5-liter containers with two plants per container during the spring and summer in a glass-covered greenhouse in Eck en Wiel, The Netherlands and under cultural practices typical of commercial Strawberry production. During the production of the plants, day temperatures ranged from 15° C. to 25° C. and night temperatures ranged from 7° C. to 14° C. Plants were one year old when the photographs and the description were taken. In the following description, color references are made to The Royal Horticultural Society Colour Chart, 2001 Edition, except where general terms of ordinary dictionary significance are used.

Botanical classification: *Fragaria* x *ananassa* 'Verdi'.

Parentage:

*Female, or seed, parent.*—Proprietary selection of *Fragaria* x *ananassa* identified as code designation E2008-001, not patented.

*Male, or pollen, parent.*—Proprietary selection of *Fragaria* x *ananassa* identified as code designation E2006-367, not patented.

Propagation:

*Type.*—By runner cuttings.

*Time to initiate roots, summer.*—About one to four days at soil temperatures about 15° C. and ambient temperatures about 17° C.

*Time to produce a rooted young plant, summer.*—About two to three weeks at soil temperatures about 15° and ambient temperatures about 17° C.

*Root description.*—Medium in thickness, fibrous; typically cream to white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Perennial; compact, upright plant habit; leaves basal; moderately vigorous growth habit; moderate growth rate; densely foliated.

*Plant height.*—About 25 cm to 35 cm.

*Plant diameter.*—About 35 cm to 40 cm.

*Stolon texture.*—Sparsely pubescent.

*Stolon color.*—Close to 145A moderately tinged with anthocyanin.

Leaf description:

*Arrangement and appearance.*—Basal rosette; compound with typically three to four leaflets per leaf; leaflets typically non-variegated, but may occasionally show a random variegated sector and leaves typically without anthocyanin when grown under normal and healthy growing conditions; slight amount of blistering observed.

*Leaflet length.*—About 10 cm to 13 cm.

*Leaflet width.*—About 7 cm to 10 cm.

*Leaflet shape*.—Broadly ovate; terminal leaflet concave in cross-section.

*Leaflet apex*.—Obtuse to acute.

*Leaflet base*.—Acute.

*Leaflet margin*.—Serrate.

*Leaflet texture and luster, upper surface*.—Pubescent; moderately glossy.

*Leaflet texture and luster, lower surface*.—Pubescent, rough; matte.

*Leaflet venation*.—Pinnate.

*Leaflet color*.—Developing leaflets, upper surface: Close to 137A. Developing leaflets, lower surface: Close to 138A. Fully expanded leaflets, upper surface: Close to between 137A and 139A; venation, close to 144C. Fully expanded leaflets, lower surface: Close to 138A; venation, close to 144C.

*Petioles*.—Length: About 15 cm to 35 cm. Diameter: About 2 mm to 4 mm. Texture, upper and lower surfaces: Pubescent; hairs orientated horizontally. Color, upper and lower surfaces: Close to 145A.

*Stipules*.—Length: Medium about 1.4 cm to 2 cm. Color: Light green becoming brown to dark brown with development.

Flower description:

*Flower form and flowering habit*.—Rotate flowers arranged singly at lateral apices; flowers held upright and at or below the foliar plane; flowers are self-fertile; about 60 to 75 flowers develop per plant during the flowering season.

*Fragrance*.—None detected.

*Natural flowering season*.—Plants flower in late April/early May in The Netherlands.

*Flower diameter*.—Medium to large, about 2.5 cm to 3.5 cm.

*Flower depth* (*height*).—About 3 mm to 5 mm.

*Petals*.—Arrangement: Single whorl of six petals; petals not imbricate. Length: About 6 mm to 9 mm. Width: About 7 mm to 10 mm. Shape: Round to broadly ovate. Apex: Rounded. Base: Attenuate. Margin: Entire. Texture, upper and lower surfaces: Smooth, glabrous; satiny. Color: When opening and fully opened, upper surface: Close to 155D. When opening and fully opened, lower surface: Close to 155D.

*Sepals*.—Arrangement and calyx description: Single whorl of 10 to 14 sepals; calyx, star-shaped; calyx adherence is slightly raised; sepals are orientated level or horizontal from the fruit; calyx diameter is slightly larger than fruit diameter. Calyx length: About 1.5 cm to 2 cm. Calyx diameter: About 2 cm to 3 cm. Length: About 1.2 cm to 1.7 cm. Width: About 3 mm to 6 mm. Shape: Lanceolate to ovate. Apex: Acute. Base: Fused. Margin: Entire. Texture, upper and lower surfaces: Pubescent. Color, upper and lower surfaces: Close to 137A.

*Peduncles*.—Length: About 7 cm to 10 cm. Diameter: About 1 mm to 2 mm. Strength: Strong. Texture: Pubescent. Color: Close to 144B.

*Pedicels*.—Length: About 3 cm to 10 cm. Diameter: About 1 mm to 2 mm. Strength: Strong. Aspect: About 90° from peduncle axis. Texture: Pubescent; hairs orientated horizontally. Color: Close to 144B.

*Reproductive organs*.—Stamens: Quantity per flower: About 25. Anther length: About 2 mm. Anther shape: Lanceolate to elliptic. Anther color: Close to 4B. Pollen amount: Abundant. Pollen color: Close to 12B. Pistils: Quantity per flower: About 30. Pistil length: About 1 mm to 2 mm. Stigma shape: Rounded. Stigma color: Close to 5A. Fruits: Quantity: About five to eleven per truss; about 60 to 75 fruits develop per plant during the fruiting season; early fruit ripening; fruit bearing non-remontant. Postharvest longevity: About seven to ten days at 7° C. Length: About 2 cm to 5 cm. Diameter: About 2 cm to 3.5 cm. Shape: Relatively, fruits are medium to large in size and are conical in shape. Fruit weight per fruit, first quality: About 17.7 g. Fruit weight per plant, first quality: About 1,070 g. Firmness: Firm. Fragrance, taste: Pleasant; good balance between sweetness and acidity; nice aroma. Degrees brix: About 8.0. Luster: Uniformly glossy. Surface unevenness: Smooth. Color, surface: Close to 43A. Color, flesh: Close to 35B. Achene density: Medium. Achene position: Level to slightly above the fruit surface. Achene weight: About 0.00051 g. Achene color: Close to 1B. Band width without achenes: Narrow.

Pathogen and pest resistance: Plants of the new Strawberry have been observed to be resistant to *Phytophthora cactorum, Sphaerotheca macularis* and *Verticillium dahliae*. To date, plants of the new Strawberry have not been observed to be resistant to pests and other pathogens common to Strawberry plants.

It is claimed:

1. A new and distinct Strawberry plant named 'Verdi' as illustrated and described.

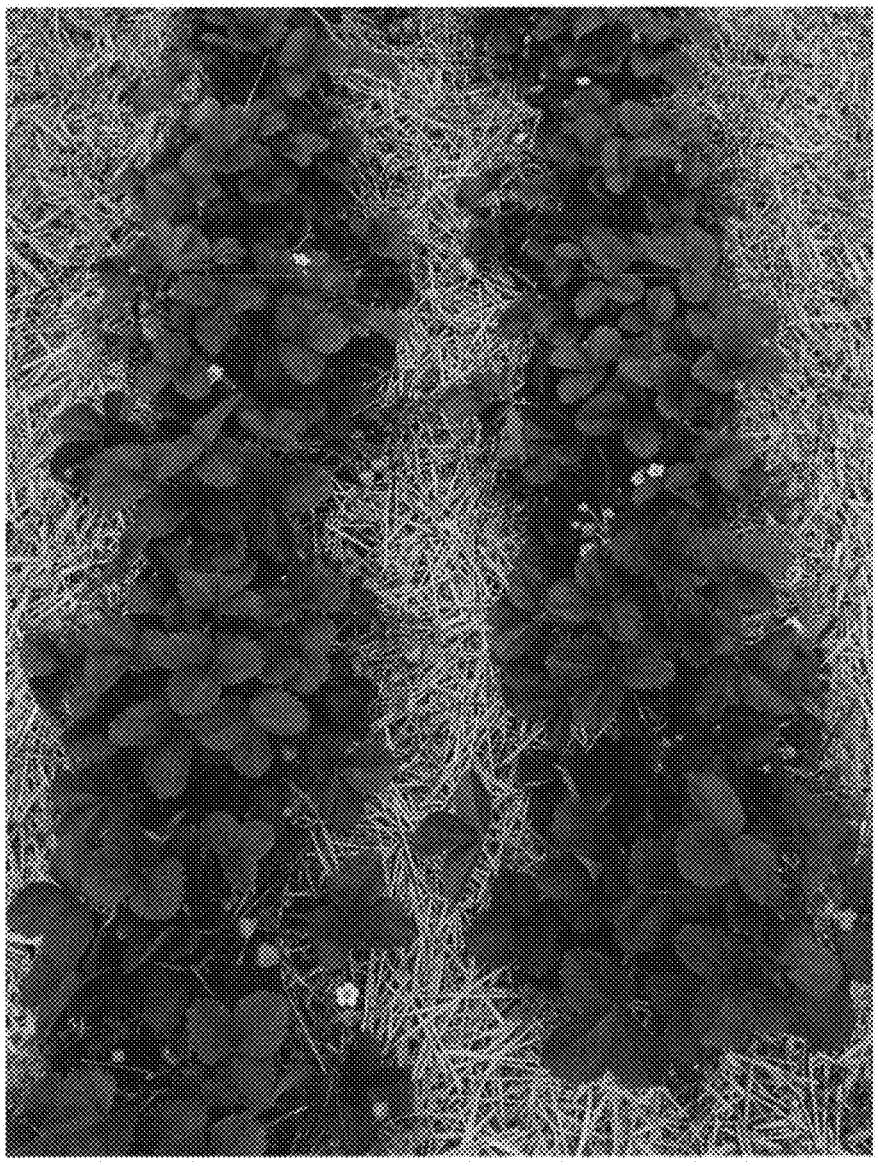

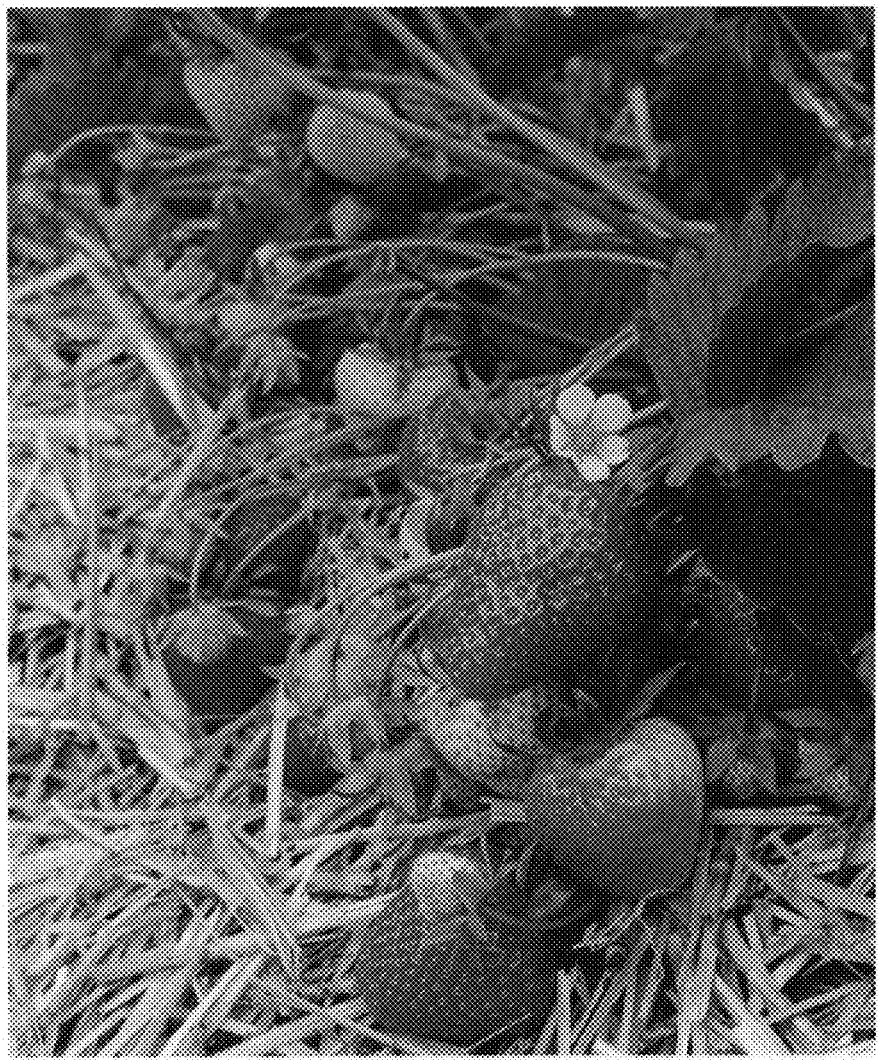

* * * * *